United States Patent [19]

Blackburn et al.

[11] Patent Number: 5,334,582

[45] Date of Patent: Aug. 2, 1994

[54] PHARMACEUTICAL BACTERIOCIN COMPOSITIONS AND METHODS FOR USING THE SAME

[75] Inventors: Peter Blackburn; Steven J. Projan, both of New York, N.Y.; Edward B. Goldberg, Newton, Mass.

[73] Assignee: Applied Microbiology, Inc., Brooklyn, N.Y.

[21] Appl. No.: 86,758

[22] Filed: Jul. 6, 1993

Related U.S. Application Data

[63] Continuation of Ser. No. 822,433, Jan. 17, 1992, abandoned, which is a continuation-in-part of Ser. No. 317,626, Mar. 1, 1989, abandoned, which is a continuation-in-part of Ser. No. 209,861, Jun. 22, 1988, abandoned.

[51] Int. Cl.$^5$ .................. A61K 37/02; A61K 31/14
[52] U.S. Cl. .................................. 514/2; 514/12
[58] Field of Search ............................ 514/2, 12

[56] References Cited

U.S. PATENT DOCUMENTS

| | | |
|---|---|---|
| 2,744,827 | 5/1956 | Mattick et al. . |
| 3,579,354 | 5/1971 | Kasik et al. . |
| 3,899,594 | 8/1975 | Nickerson et al. . |
| 3,988,307 | 10/1976 | Gross . |
| 4,158,607 | 6/1979 | Kalinowski et al. . |
| 4,318,928 | 3/1982 | Sing . |
| 4,477,471 | 10/1984 | Gonzalez . |
| 4,485,029 | 11/1984 | Kato et al. ............ 252/106 |
| 4,584,199 | 4/1986 | Taylor . |
| 4,597,972 | 7/1986 | Taylor . |
| 4,716,115 | 12/1987 | Gonzalez et al. . |

FOREIGN PATENT DOCUMENTS

| | | |
|---|---|---|
| 0384319 | 8/1990 | European Pat. Off. . |
| 738655 | 10/1955 | United Kingdom . |
| 8912399 | 12/1989 | World Int. Prop. O. . |

OTHER PUBLICATIONS

Chemical Abstracts, vol. 77 (1972), p. 14; vol. 82 (1975) p. 94, vol. 86 (1977), p. 58; vol. 89 (1978) pp. 64–65.
Reisinger et al., *Arch. Microbiol.*, vol. 127, pp. 187–193 (1980).
Hurst, *Advances in Applied Microbiology* 27; 85–123 (1981).
Morris et al., *J. Biol. Chem*, vol. 259, pp. 13590–13594 (1984).
Ruhr et al, *Antimicrob. Agents Chemother*, vol. 27, pp. 841–845 (1985).
Tsai et al, *Appl. Environ. Microbiol*, vol. 53, pp. 352–357 (1987).
"Focus on Nisin", *Food Manufacture*, Mar. 1987, pp. 63–64.
"A Natural Preservative" *Food Eng. Int'l.*, May 1987, pp. 37–38.
Zygmunt et al. "Lysostaphin: Model for a Specific Enzymatic Approach to Infectious Disease", *Progress in Drug Research* 16, 1972, pp. 309–333.
Claypool et al. *Journal of Dairy Science* 49, 314–315 (1966).
Cowell et al., *J Appl. Bact.* 34 (4), 787–791 (1971).
Johnson et al., *J Appl. Bact.* 45 (1978), pp. 99–109.
"The Food Preservative Nisaplin—Technical Data".
*Federal Register*, vol. 47, No. 101, May 25, 1982.
Kordel et al., *FEB* 06784, vol. 244, No. 1, Feb. 1989, pp. 99–102.
Weber et al., "Quaternary Ammonium Compounds," *Soap & Sanitary Chemicals*, Sep. 1948, pp. 137–142.
J. Roger Hart, "Chelating Agents As Preservative Potentiators", W. R. Grace & Co., 323–337 (1984).

*Primary Examiner*—Michael G. Wityshyn
*Assistant Examiner*—Choon P. Koh
*Attorney, Agent, or Firm*—White & Case

[57] ABSTRACT

Compositions comprising lanthionine-containing bacteriocins such as nisin in combination with a chelator act as bactericides in low pH environments. In a preferred embodiment pharmaceutical preparations containing the compositions are used for the control of bacteria responsible for disorders of the gastrointestinal tract.

26 Claims, No Drawings

PHARMACEUTICAL BACTERIOCIN COMPOSITIONS AND METHODS FOR USING THE SAME

This application is a continuation of application Ser. No. 07/822,433, filed Jan. 17, 1992 now abandoned, which is a continuation-in-part of U.S. Ser. No. 07/317,626, filed Mar. 1, 1989 (abandoned), which was a continuation-in-part of U.S. Ser. No. 07/209,861, filed Jun. 22, 1988 (abandoned).

BACKGROUND AND SUMMARY OF THE INVENTION

The antimicrobial activity of the lanthionine-containing bacteriocin nisin is restricted towards certain gram positive organisms and is optimal at pH 5.0. The antimicrobial activity of nisin is enhanced when used in combination with a chelator such as EDTA. The activity of the nisin chelator compositions have been found to be significantly greater or optimal at a pH greater than 5.0. For example, it has been determined that the antimicrobial activity towards *Staphylococcus aureus* of a nisin and EDTA composition is significantly greater at pH 8.0 than the activity of the same composition against *S. aureus* at pH 5.0 The combination of a chelator with nisin was also found to result in activity towards gram negative bacteria, an activity which is not inherent in nisin.

The present invention concerns lanthionine-containing bacteriocin compositions which are active in acidic pH below 5.0 and display considerable activity against gram negative bacteria. These low-pH-active compositions may be useful for example in methods of treating or preventing infections or growth of microorganisms in the gastrointestinal tract of humans and animals. These compositions when introduced into the gastrointestinal tract will act as bactericides even in the low-pH environment of the stomach. This antibacterial activity may be useful in containing the growth of infections caused by gastrointestinal pathogens such as species of Helicobacter, Escherichia, Salmonella, Bacillus, Clostridia, Bacteroides, Campylobacter and Yersinia. Such low-pH active bacteriocin compositions would therefore be useful in the treatment of various diseases or symptoms due to the presence of such pathogenic bacteria.

Various gastrointestinal diseases or symptoms including diarrhea, gastritis, peptic and duodenal ulcer, and gastric carcinoma are due to the presence of pathogenic microorganisms in the gastrointestinal tract. Escherichia and Salmonella, in particular, but also certain species of Clostridia, Bacillus, Bacteroides, Campylobacter and Yersinia can be responsible for diarrhea especially in neonatal farm animals. (R.E. Holland, 1990, *Clin. Microbiol. Rev.* 3:345, "Some infectious causes of diarrhea in young farm animals.") *Helicobacter pylori* are implicated in gastritis, duodenal and peptic ulcer disease. (Peterson, W.L., 1991, *New Eng. J. Med.* 324: 1043, "Helicobacter pylori and peptic ulcer disease") and are also associated with gastric carcinoma. (Henderson, B.E., Ross, R.K., and Pike, M.C., 1991, *Science* 254:1131, "Toward the primary prevention of cancer," Nomura, A. Stemmermann, G.A., Chyou, P.H., Kato,I., Perez-Perez, G. and Blaser, M.J. (1991) *New Eng. J. Med.* 325: 1132 "*Helicobacter pylori* infection and gastric carcinoma among Japanese Americans in Hawaii."; Parsonnet, J., Friedman, G.D., Vandersteen, D.P., Chang, Y., Vogelman, J.H., Orentreich,N, and Sibley, R.K. (1991) *New Eng. J. Med.* 325:1127; Forman, D., Sitas, F., Newell, D.G., Stacey, A.R., Boreham, J., Peto, R., Campbell, T.C., Li, J. and Chen, J. (1990) *Int. J. Cancer* 46:608 "Geographic association of Helicobacter pylori antibody prevalence and gastric cancer mortality in rural China").

Many gastrointestinal pathogens are gram negative bacteria, organisms against which nisin would be expected to be inactive. (Hurst, A. , 1981, "Nisin," *Adv. in App. Micr.* V. 27 , p. 85–121. ) For example, *Helicobacter pylori* (which has also been identified in the prior art as *Campylobacter pylori*) is a gram negative microaerophilic bacillus that colonizes the gastric mucosa. Since 1983, when first reported in association with histologic gastritis, a relationship between suppression of *H. pylori* infection and improvement of gastric disorders has been noted. However, although numerous antibiotics have been tried against *H. pylori* infection, none have so far proved acceptable and no agent or regimen has been approved for use against this organism. Long term eradication of the organism has seldom been achieved and antibiotics themselves can produce unacceptable side effects. (Peterson, W.L., 1991, *New Eng. J. Med.* 324:1043 "*Helicobacter pylori* and peptic ulcer disease"; Warren, J.R., 1983, Lancet 1:1273, "Unidentified curved bacilli on gastric epithelium in active chronic gastritis"; Morgan et al., 1988, *Gastroenterology* 95:1178, "Nitrofurans in the treatment of gastritis associated with *Campylobacter pylori*"; Glupczynski, Y. et al., 1988, *Am. J. Gastroenterol.* 83:365 "*Campylobacter pylori*-associated gastritis: a double-blind placebo controlled trial with amoxycillin"; Rauws, E.A. et al., 1988, *Gastroenterology* 94:33, "*Campylobacter pylori*-associated chronic antral active gastritis"; Glupczynski, Y. 1990 in *Helicobacter pylori*, gastritis, and peptic ulcer"; Malfertheiner, P., Ditschuneit, H., Eds. Springer-Verlag, Berlin, Germany pp 49–58; Rauws, E.A. and Tytgat, G.N. 1990 Lancet 335:1233 "Cure of duodenal ulcer associated with eradication of *Helicobacter pylori*". O'Riordan, T. et al. , 1990, *Gut* 31:999 "Adjuvant antibiotic therapy in duodenal ulcers treated with colloidal bismuth subcitrate"; Weil, J. et al. , 1990, *Aliment. Pharmacol. Ther.*, 4:651 "Helicobacter pylori infection treated with a tripotassium dicitrato bismuthate and metronidazole combination"; Coghlan, J.G., Gilligan, D., Humphries, H., et al., 1987, Lancet 2:1109 "*Campylobacter pylori* and recurrence of duodenal ulcer —a 12-month follow-up study"; Marshall, B.J. Goodwin, C.S., Warren, J.R. et al., 1988, *Lancet* 2:1437, "Prospective double-blind trial of duodenal ulcer relapse after eradication of *Campylobacter pylori*").

The present invention concerns pharmaceutical compositions comprising a lanthionine-containing bacteriocin such as nisin and a chelating agent with a suitable carrier for use in low-pH environments as bactericides. These compositions are stable and active at acidic pH and are useful for their antibacterial activity against gram negative bacteria in low-pH environments such as encountered in the gastrointestinal tract. Pharmaceutical nisin compositions according to the invention act quickly, so that when delivered into the stomach and gastrointestinal tract their activity should not be limited by the clearance rate of the stomach contents. Furthermore, unlike antibiotics, nisin compositions can be safely ingested. The pharmaceutical compositions may be used alone in treatment regimens or in combination with other pharmaceutical agents or drugs. The invention also concerns methods of using and making such compositions.

DETAILED DESCRIPTION OF THE INVENTION

The efficacy of the present invention has been demonstrated on *E. coli* bacteria which are found in the mammalian gut and are frequently responsible for gastrointestinal disorders. The survival of *E. coli* is unaffected by exposure to EDTA or citrate by themselves or by exposure to nisin by itself. In addition, suspensions of *E. coli* exposed to acid survive well in an acidic environment until the pH drops below pH 2.5. However, as is set forth below, when nisin is combined with EDTA at a range of acidic pH values, significant reduction in the viability of the bacteria was seen after only 1 minute of exposure to the nisin compositions. At pH 3.5, a reduction by more than 6 logarithms in the viable count of bacteria can be achieved after only 1 minute exposure to the nisin-chelator composition. Below pH 3.5 some reduction of the potency of the nisin compositions is apparent but, nevertheless, an approximately 1000-fold enhancement of nisin activity remains even at pH 2.5 (Table 1).

EDTA-activated nisin is bactericidal towards *E. coli* in the presence of various acid vehicles including acetate, citrate, lactate, and succinate, as shown in Tables 2-5. As illustrated by results obtained at pH 3.5, the rapid bactericidal activity of the nisin compositions can be influenced by the choice of acid vehicle. In all the illustrated cases, as the concentration of each acid anion is increased, the bactericidal activity of the nisin compositions is observed to decrease. Nevertheless, each of these acid vehicles is suitable for the expression of chelator-enhanced nisin activity. Exposure of the bacteria to these nisin compositions for a longer period than that illustrated below is expected to be effective in reducing the number of bacteria even when the formulations contain the less effective acid vehicles.

Evaluation of Germicidal Activity of Chelator-Enhanced Nisin in Acid Vehicles towards Gram Negative Bacteria The rapid activities of various chelator-enhanced nisin formulations were evaluated in acid vehicles in a germicidal suspension assay.

*E. coli* cells from an overnight Trypticase soy nutrient agar (TSA) were resuspended to a density measured as an absorbance of 1.0 at 600 nm in sterile ddH$_2$O. The reaction of the cells with each of the bactericidal test formulations analyzed is started by addition of 30 μl of cells to 970 μl of test formulation. The reaction mixture was incubated at 37° C. for at least 1 minute and then centrifuged in a microfuge for 1 minute. The cell pellet was washed by resuspension in 1 ml of neutralization buffer. (The neutralization buffer: 50 mM Tris-HCl, pH 7.0, 5 mM MgSO$_4$, 20 mM CaCl$_2$, 0.1 M NaCl and 0.1% gelatin was prepared by first making Tris buffer and adjusting the pH. The salts and gelatin were then added and the solution stirred with heat until the solution was clear. The solution was then autoclaved for 20 min. The neutralization buffer was used without dilution.) The cells were centrifuged in a microfuge for 1 minute and resuspended in 1 ml of neutralization buffer. The viable count was determined by spreading 100 μl of bacterial suspension and serial dilutions thereof in neutralization buffer on nutrient agar and scoring surviving colonies after 24 h at 37° C. Percent survival relative to untreated controls was calculated from the scored values.

EDTA-enhanced activity of nisin is expressed at low pH. Below pH 3.5 the degree of enhancement is reduced, presumably as the carboxyl groups of the chelator are titrated. Nevertheless, an approximately 1000-fold enhancement of nisin by EDTA was observed even at pH 2.5. See results presented in Table 1.

TABLE 1

EDTA activation of Nisin towards *Escherichia coli*
Dependence with respect to acidic pH

| EDTA mM | Nisin μg/ml | 7.0 | 2.0 | 2.5 | 3.0 | 3.5 | 4.0 |
|---|---|---|---|---|---|---|---|
| | | | | % survival at 1 min[a] | | | |
| 0 | 0 | 100 | — | — | — | 100 | — |
| 0 | 100 | — | 0.28 | 3.37 | 4.43 | 100 | 100 |
| 1.0 | 0 | — | 0.07 | — | 5.41 | — | — |
| 1.0 | 100 | — | 0.01 | 0.005 | 0.0007 | <10$^{-4}$ | <100$^{-4}$ |

[a]Initial viable count 4 × 10$^7$ colony forming units /ml
[b]Incubations performed at 37° C. in 20 mM Na acetate buffer adjusted to pH

TABLE 2

Chelator Activation of Nisin-Acetate towards *Escherichia coli*
Dependence with respect to Acetate concentration

| EDTA mM | Nisin μg/ml | 0 | 0.1 | 0.3 | 1.0 | 3.0 |
|---|---|---|---|---|---|---|
| | | | (% w/v) Acetate pH 3.5 | | | |
| | | | % survival at 1 min[a] | | | |
| 0 | 0 | 100 | 55 | 80 | 90 | 10.1 |
| 0 | 100 | — | 9.6 | 70 | 100 | 100 |
| 1.0 | 0 | — | 40 | 25 | 25 | 10.7 |
| 1.0 | 100 | — | 0.0005 | <10$^{-4}$ | 0.02 | 0.4 |

[a]Initial viable count 2 × 10$^7$ colony forming units /ml
[b]Incubations performed at 37° C.

TABLE 3

Chelator Activation of Nisin-Citrate towards *Escherichia coli*
Dependence with respect to Citrate concentration

| EDTA mM | Nisin μg/ml | 0 | 0.1 | 0.3 | 1.0 | 3.0 |
|---|---|---|---|---|---|---|
| | | | (% w/v) Citrate pH 3.5 | | | |
| | | | % survival at 1 min[a] | | | |
| 0 | 0 | 100 | 100 | 56.3 | 72.9 | 100 |
| 0 | 100 | — | 0.003 | 0.0007 | 0.56 | 14.6 |
| 1.0 | 0 | — | 100 | 50.0 | 47.9 | 100 |
| 1.0 | 100 | — | 0.0006 | 0.0002 | 0.69 | 20.8 |

[a]Initial viable count 5 × 10$^7$ colony forming units /ml
[b]Incubations performed at 37° C.

TABLE 4

Chelator Activation of Nisin-Lactate towards *Escherichia coli*
Dependence with respect to Lactate concentration

| EDTA mM | Nisin μg/ml | 0 | 0.1 | 0.3 | 1.0 | 3.0 |
|---|---|---|---|---|---|---|
| | | | (% w/v) Lactate pH 3.5 | | | |
| | | | % survival at 1 min[a] | | | |
| 0 | 0 | 100 | 22.2 | 46.7 | 35.6 | 4.2 |
| 0 | 100 | — | 4.4 | 0.24 | 17.8 | 26.7 |
| 1.0 | 0 | — | 5.1 | 0.46 | 0.91 | 1.58 |
| 1.0 | 100 | — | <10$^{-4}$ | 0.02 | 0.20 | 2.84 |

[a]Initial Viable count 5 × 10$^7$ colony forming units /ml
[b]Incubations performed at 37° C.

TABLE 5

Chelator Activation of Nisin-Succinate towards *Escherichia coli*
Dependence with respect to Succinate concentration

| EDTA mM | Nisin μg/ml | 0 | 0.1 | 0.3 | 1.0 | 3.0 |
|---|---|---|---|---|---|---|
| | | | (% w/v) Succinate pH 3.5 | | | |
| | | | % survival at 1 min[a] | | | |
| 0 | 0 | 100 | 85.5 | 29.9 | 36.7 | 13.9 |
| 0 | 100 | — | 18.3 | 66.6 | 83.4 | 28.4 |
| 1.0 | 0 | — | 56.8 | 63.6 | 46.2 | 43.2 |

TABLE 5-continued

Chelator Activation of Nisin-Succinate towards *Escherichia coli* Dependence with respect to Succinate concentration

| EDTA mM | Nisin μg/ml | (% w/v) Succinate pH 3.5 | | | | |
|---|---|---|---|---|---|---|
| | | 0 | 0.1 | 0.3 | 1.0 | 3.0 |
| | | % survival at 1 min$^a$ | | | | |
| 1.0 | 100 | — | 0.02 | 6.21 | 14.2 | 4.73 |

$^a$Initial viable count $3.4 \times 10^6$ colony forming units /ml
$^b$Incubations performed at 37° C.

At pH 3.5 EDTA-enhanced nisin activity was observed in the presence of all acid anions tested (see Tables 2–5). At pH 3.5, lactate at 0.3% was somewhat inhibitory to EDTA-enhanced nisin activity. Nevertheless the activity is still enhanced more than 1000-fold over 0.3% lactate alone and 0.1% lactate is not inhibitory to EDTA-enhanced nisin.

At pH 3.5, up to 0.3% acetate and 0.3% citrate appear compatible with chelator-enhanced nisin germicidal activity towards *E. coli* suspensions. These anions appear to show the most promise as acid vehicles to be formulated with EDTA-enhanced nisin. Citrate is a most suitable acid vehicle for EDTA-enhanced nisin compositions. Citrate is a naturally occurring food substance and intermediary metabolite and an effective enhancer of nisin bactericidal activity in its own right (Table 3). Nisin-citrate compositions can be expected to be safe and effective for containing or eliminating the growth of undesirable microorganisms in the gastrointestinal tract of humans and animals.

As demonstrated, nisin by itself is ineffective towards gram negative bacteria. Moreover, citrate is a metabolite, it does not inhibit the growth of bacteria and bacteria grow well on nutrient agar supplemented with citrate. However, nisin in the presence of citrate is active against gram negative bacteria. Thus, it is possible to demonstrate the activity of nisin towards gram negative bacteria by performing growth inhibition assays on nutrient agar supplemented with various concentrations of citrate. This nisin-citrate agar assay has much more general applicability. The assay provides a method for screening potential agents other than citrate in combination with nisin for their potential properties as enhancers of nisin's inherent bactericidal activity.

*E. coli* is resuspended to an optical density of 1.0 at $A_{600}$. A 100 μl sample of the bacterial suspension is spread uniformly on Trypticase Soy nutrient agar (TSA) supplemented with various concentrations of citrate (eg. 0.1%, 0.3%, 1.0%, 3.0%) and incubated for 1 hour at 37° C. A nisin stock solution and serial dilutions thereof in 0.1% bovine serum albumin (BSA), are prepared and 5 μl are taken from each and deposited onto the growing bacterial lawn. The TSA plates are then incubated for 24 hours at 37° C. After 24 hours at 37° C., *E. coli* grown on TSA supplemented with citrate form a confluent lawn. The activity of nisin towards bacteria grown in the presence of citrate is demonstrated by clear zones in the bacterial lawn where the serially diluted nisin samples were deposited. The effectiveness of nisin against the gram negative bacteria can be assessed from determining the minimum amount of nisin required to produce a clear zone of growth inhibition. As the concentration of citrate in the nutrient agar is increased, less nisin is required to inhibit the growth of *E. coli*, as is illustrated by the data shown in Table 6.

TABLE 6

The activity of Nisin towards *E. coli* grown on Nutrient Agar in the presence of Citrate

| % Citrate | Nisin NIC[1] |
|---|---|
| 0% | 3,333 μg/ml |
| 0.1% | 370 μg/ml |
| 0.3% | 123 μg/ml |
| 1.0% | 13.7 μg/ml |
| 3.0% | 0.06 μg/ml |

[1]Nominal inhibitory concentration of nisin minimally required to prevent growth of *E. coli* strain ATCC8739 grown on Trypticase Soy Agar supplemented with the various concentrations of citrate as indicated.

The activity of nisin enhanced with EDTA citrate or other chelators can also be demonstrated towards *Helicobacter pylori* by the germicidal suspension assay. Freshly grown *H. pylori* cells which may be grown on a nutrient agar plate (Trypticase Soy Agar, BBL 11043, supplemented with 5% defibrinated sheep blood) are harvested and subsequently grown at 37° C. for 72 hours in an anaerobe jar using a Campylobacter microaerophilic gas generator (BBL71034). The cells should then be resuspended to a cell density of 1.0 $A_{600}$ to provide a suitable stock suspension. The assay may be started by addition of 30 μl of bacterial suspension 970 μl of test solution, incubated for at least 1 minute and then centrifuged for 1 minute in a microfuge. The cell pellet should be washed by resuspension in 1 ml of sterile neutralization buffer, resuspended again and then serially diluted in neutralization buffer. The viable count may be determined by spreading 100 μl of bacterial suspension and dilutions thereof on nutrient agar and scoring surviving colonies after 72 hours incubation at 37° C. in the modified atmosphere described above. Percent survival relative to untreated controls may be calculated from the scored values.

The activity of nisin enhanced with EDTA, citrate or other chelators can also be demonstrated towards species of Salmonella by the germicidal suspension assay. Freshly grown *S. typhimurium* cells are taken from a nutrient agar plate (Trypticase Soy Agar, BBL11043,) grown at 37° C. for 24 hours. The cells are resuspended to a cell density of 1.0 $A_{600}$ to provide a suitable stock suspension. The assay is started by addition of 30 μl of bacterial suspension to 970 μl of test solution and incubated for at least 1 minute and then centrifuged for 1 minute in a microfuge. The cell pellet is washed by resuspension 1 ml of sterile neutralization buffer, resuspended again and then serially diluted in neutralization buffer. The viable count is determined by spreading 100 μl of bacterial suspension and dilutions thereof on nutrient agar and scoring surviving colonies after 24 hours incubation at 37° C. Percent survival relative to untreated controls is calculated from the scored values.

The low-pH-active bacteriocin compositions of the invention are preferably administered orally in the form of a pharmaceutical preparation which contains an effective amount of the lanthionine-containing bacteriocin, an effective amount of a chelating agent, an acid vehicle and a pharmaceutically acceptable carrier. The lanthionine-containing bacteriocin may be selected from the group consisting of nisin, subtilin, epidermin, Pep 5, ancovenin, gallidermin, duromycin or cinnamycin. Suitable chelating agents include, but are not limited to, EDTA, CaEDTA, CaNa$_2$ EDTA and other alkyldiamine tetracetates as well as citrate. In certain instances the chelator and the acid vehicle can be the same, such as when the acid vehicle and the chelator are both citrate. Suitable acid vehicles for use in the compositions of this invention are acetate, propionate, citrate, lactate, succinate, fumarate, malonate, adipate, sorbate, phosphate and ascorbate.

The compositions of the invention are also effective at slightly acid pH levels, (e.g., pH 5.0 and even higher pH levels, (e.g., pH 8.0), against pathogenic bacteria which may inhabit the gastrointestinal tract, such as *E. coli* and *S. typhimurium* as disclosed in copending application Ser. No. 317,626. The disclosure of application Ser. No. 317,626 is hereby incorporated by reference in its entirety.

The pharmaceutical compositions of the invention may thus also be formulated as antacid compositions or administered in combination with an antacid wherein the administration would result for instance in a higher stomach pH environment than that existing prior to administration. The nisin chelator compositions would still be effective against the pathogenic bacteria under such conditions.

The pharmaceutically acceptable carrier may be in the form of a solid, semi-solid or liquid diluent or a capsule. In certain embodiments of the invention the acid vehicle and the pharmaceutical carrier may be the same. Other pharmaceutically acceptable carriers may be cellulose derivatives, gelatin, lactose, starch, etc.

The pharmaceutical compositions may be in the form of solutions, colloids or emulsions, powders, tablets, capsules or gels.

The dry forms of the low pH compositions may be pressed into tablets which may be coated with a concentrated solution of sugar and which may contain other pharmaceutically acceptable substituents such as gum arabic, gelatin, talc, or titanium dioxide and may be also coated with various dyes. Hard gelatin capsules may be prepared which contain granules of the bacteriocin, acid vehicle and chelating agent in combination with a solid, carrier such as lactose, potato starch, corn starch, cellulose derivatives or gelatin.

Liquid preparations for oral administration may be prepared in the form of syrups or suspensions comprising the peptide bacteriocin, the chelating agent, the acid vehicle, and sugar, water and glycerol or propylene glycol. If desired, such liquid preparations may contain coloring agents, flavoring agents, sweeteners such as saccharin and thickening agents such as cellulose derivatives.

Delivery of a dosage could obviously be achieved by modifications of the simple aqueous formulations by inclusion of thickeners, emulsifiers, or particulates to effect a colloidal suspension. Alternatively, osmotically balanced solutions containing a suitable dosage could be administered in volumes as little as 10 ml or as large as 4 liters. Osmotically balanced solutions such as those used as gastrointestinal lavage solutions would be suitable (Di Palma, J.A. and Brady, C.E., 1989, Am. J. Gastroenterol. 84:1008, "Colon Cleansing for Diagnostic and Surgical Procedures: Polyethylene glycol Lavage Solution"; Di Palma, J.A. and Marshal, J.B., 1990, Gastrointestinal Endoscopy 1990, 36:285, "Comparison of a new Sulfate-free Polyethylene glycol Electrolyte Lavage Solution versus a Standard Solution for Colonoscopy Cleansing"; Fordtran, J.S., et al., 1990, Gastroenterol. 98:11, "A low-Sodium Solution for Gastrointestinal Lavage"). The performance of gastrointestinal lavage solutions used to cleanse the gastrointestinal tract would be expected to be improved by inclusion of the germicidal compositions described herein.

The typical daily dose of the inventive compositions may vary according to the pathogenic microorganism infection being treated, the site of infection, and the symptoms of the disease being treated. In general, it is expected that oral dosages would range from 0.1 mg per dose to 300 mg per dose of lanthionine-containing bacteriocin substance, and 0.1 g per dose to 30 g per dose of chelator.

For example, since the volume of stomach contents varies as a function of the time lapsed after the last meal, simple aqueous formulations suitable for gastrointestinal use may be prepared as follows:

For a final concentration to be achieved in the stomach at 0.1% citrate + 0.001% nisin (10 ug/ml) delivered in 10 ml and assuming approximately 100 ml in stomach:

| Dosage 1: 1.0 mg nisin and 0.1 g citrate | |
|---|---|
| Na citrate | 1.0% |
| nisin | 0.01% |
| saccharin | 0.005% |
| polysorbate 20 | 1.0% |
| glycerol | 10.0% |
| water | 87.985% |

For a final concentration to be achieved in the stomach at 3.0% citrate + 0.03% nisin (300 ug/ml) delivered in 10 ml and assuming 100 ml in stomach:

| Dosage 2: 30 mg nisin and 3.0 g citrate | |
|---|---|
| Na citrate | 30.0% |
| nisin | 0.3% |
| saccharin | 0.005% |
| polysorbate 20 | 1.0% |
| glycerol | 10.0% |
| water | 57.695% |

For a final concentration to be achieved in the stomach at 0.1% citrate + 0.001% nisin (10 ug/ml) delivered in 10 ml and assuming 1000 ml in stomach:

| Dosage 3: 10 mg nisin and 1.0 g citrate | |
|---|---|
| Na citrate | 10.0% |
| nisin | 0.1% |
| saccharin | 0.005% |
| polysorbate 20 | 1.0% |
| glycerol | 10.0% |
| water | 77.895% |

For a final concentration to be achieved in the stomach at 3.0% citrate + 0.03% nisin (300 ug/ml) delivered in 100 ml and assuming 1000 ml in stomach:

| Dosage 4: 300 mg nisin and 30 g citrate | |
|---|---|
| Na citrate | 30.0% |
| nisin | 0.3% |
| saccharin | 0.005% |
| polysorbate 20 | 1.0% |
| glycerol | 10.0% |
| water | 57.695% |

For a final concentration to be achieved in the stomach at 3.0% citrate + 0.03% nisin (300 ug/ml) delivered in 100 ml and assuming 100 ml in stomach:

| Dosage 5: 60 mg nisin and 6.0 g citrate | |
| --- | --- |
| Na citrate | 6.0% |
| nisin | 0.06% |
| saccharin | 0.005% |
| polysorbate 20 | 1.0% |
| glycerol | 10.0% |
| water | 82.935% |

It is also contemplated that depending on the type of pathogenic microorganism and disease being treated, the treatment regimen may comprise other drugs and pharmaceutical agents either as part of the pharmaceutical composition being administered or in treatment regimens which combine both the low-pH-active bacteriocin composition and another drug effective for treating the gastrointestinal tract. For example, in the treatment of diarrhea which may be caused by infections of a pathogenic microorganism such as one of the species of Salmonella, the low-pH bacteriocin composition may be administered in a pharmaceutical preparation which also contains kaolin, pectin, or some other binding agent. Such symptoms may also be treated by the concurrent administration of the low-pH bacteriocin composition and the binding agent. In addition, antacid formulations may be used in such treatment regimens and it is not expected that the antacid will affect the activity of the nisin-chelator composition.

In treating infections of the pathogenic microorganism *Helicobacter pylori*, the low-pH bacteriocin composition may be administered in connection with another pharmaceutically active substance against *H. pylori* such as a bismuth salt, e.g., bismuth subcitrate or bismuth subsalicylate. The inventive compositions may be administered in connection with other agents such as cimetidine, ranitidine, omeprazole, antacids, urease inhibitors or combinations thereof in order to treat some of the diseases and symptoms associated with the presence of *H. pylori* in the gastrointestinal tract. It is contemplated that in these therapies the active pharmaceutical agents may be administered concurrently or intermittently with the inventive pharmaceutical compositions and the mode of administration may be varied during the course of the treatment as required.

We claim:

1. A method of preventing or treating for bacterial infection in a low-pH environment in the range of pH 2-5 comprising contacting the bacteria with a composition comprising a lanthionine-containing bacteriocin and a chelating agent in a pharmaceutically acceptable carrier.

2. The method of claim 1 wherein the chelating agent is citrate.

3. The method of claim 1 wherein the chelating agent is EDTA.

4. The method of claim 1 wherein the chelating agent comprises citrate and EDTA.

5. A method of claim 1 wherein the composition also contains acetate, succinate or lactate.

6. The method of claim 1, wherein the bacteriocin is selected from the group consisting of nisin, subtilin, epidermin, Pep 5, ancovenin, gallidermin, duromycin or cinnamycin.

7. The method of claim 1 wherein the bacteriocin is nisin and the chelator is citrate.

8. The method of claim 1, wherein the composition also comprises an acid vehicle.

9. The method of claim 8, wherein the acid vehicle is selected from the group consisting of acetate, propionate, citrate, lactate, succinate, fumarate, malonate, adipate, sorbate, phosphate, or ascorbate.

10. A method of preventing or treating a bacterial infection in the gastrointestinal tract comprising administering into the gastrointestinal tract a composition comprising a lanthionine-containing bacteriocin and a chelating agent.

11. The method of claim 10, wherein the lanthionine-containing bacteriocin is nisin.

12. The method of claim 10 wherein the chelating agent is citrate.

13. The method of claim 10 wherein the bacteria are gram negative bacteria.

14. A method of treating gastrointestinal disorders in mammals due to the presence of *Escherichia coli* bacteria comprising contacting the bacteria with a composition comprising nisin and a chelating agent in a pharmaceutically acceptable carrier.

15. A method of treating gastrointestinal disorders in mammals due to the presence of *Helicobacter pylori* bacteria comprising contacting the bacteria with a composition comprising nisin and a chelating agent in a pharmaceutically acceptable carrier.

16. A method of treating gastrointestinal disorders in mammals due to the presence of Salmonella bacteria comprising contacting the bacteria with a composition comprising nisin and a chelating agent in a pharmaceutically acceptable carrier.

17. A pharmaceutical composition useful for treating gastrointestinal disorders due to gram negative bacteria comprising a suitable amount of nisin, a chelating agent, an acid vehicle, and a pharmaceutically acceptable carrier.

18. The pharmaceutical composition of claim 17 wherein the chelating agent is EDTA and the acid vehicle is citrate.

19. A pharmaceutical composition useful for treating gastrointestinal disorders due to microorganisms comprising an effective amount of a lanthionine-containing bacteriocin, a chelator, an acid vehicle and a pharmaceutically acceptable carrier.

20. The composition of claim 19, wherein the bacteriocin is selected from the group consisting of nisin, subtilin, epidermin, Pep 5, ancovenin, gallidermin, duromycin or cinnamycin.

21. The composition of claim 20, wherein the chelator and the acid vehicle are citrate.

22. The composition of claim 21, wherein the chelator is EDTA and the acid vehicle is citrate.

23. A method for inhibiting the growth of or killing bacteria in a low-pH environment in the range of pH 2-5 comprising contacting the bacteria with a composition comprising a lanthionine-containing bacteriocin and a chelating agent in a suitable carrier.

24. The method of claim 23 wherein the bacteria are gram negative.

25. The method of claim 23 wherein the bacteriocin is nisin.

26. The method of any one of claims 23-25 wherein the pH range is 2-4.

* * * * *